United States Patent
Oguchi et al.

(10) Patent No.: US 11,981,622 B2
(45) Date of Patent: May 14, 2024

(54) METHOD FOR PRODUCING ALCOHOL AND CATALYST FOR PRODUCING ALCOHOL

(71) Applicant: SHOWA DENKO K.K., Tokyo (JP)

(72) Inventors: Wataru Oguchi, Oita (JP); Gen Inoue, Oita (JP); Toshihiro Kimura, Oita (JP); Masafumi Koyano, Oita (JP); Takuya Kuzutani, Oita (JP)

(73) Assignee: Resonac Corporation, Tokyo (JP)

(*) Notice: Subject to any disclaimer, the term of this patent is extended or adjusted under 35 U.S.C. 154(b) by 508 days.

(21) Appl. No.: 17/288,382

(22) PCT Filed: Oct. 28, 2019

(86) PCT No.: PCT/JP2019/042212
§ 371 (c)(1),
(2) Date: Apr. 23, 2021

(87) PCT Pub. No.: WO2020/090756
PCT Pub. Date: May 7, 2020

(65) Prior Publication Data
US 2021/0380509 A1 Dec. 9, 2021

(30) Foreign Application Priority Data
Nov. 2, 2018 (JP) ................. 2018-207344

(51) Int. Cl.
*C07C 29/17* (2006.01)
*B01J 21/08* (2006.01)
(Continued)

(52) U.S. Cl.
CPC ............. *C07C 29/172* (2013.01); *B01J 21/08* (2013.01); *B01J 23/30* (2013.01); *B01J 35/615* (2024.01);
(Continued)

(58) Field of Classification Search
CPC ....... C07C 29/04; C07C 31/08; C07C 29/172; B01J 21/08; B01J 23/30; B01J 35/1019;
(Continued)

(56) References Cited

U.S. PATENT DOCUMENTS 2,173,187 A * 9/1939 Tanner .................... C07C 29/04
568/896
3,686,334 A * 8/1972 Britton .................... C07C 29/04
568/896
(Continued)

FOREIGN PATENT DOCUMENTS

CN 1130103 A 9/1996
CN 111065618 A 4/2020
(Continued)

OTHER PUBLICATIONS

Brame, J. et al., Surface area analysys using the Brunauer-Emmett-Teller (BET) method, ERDC Innovative Solutions, 23 pages. (Year: 2016).*
(Continued)

*Primary Examiner* — Yate' K Cutliff
(74) *Attorney, Agent, or Firm* — Sughrue Mion, PLLC

(57) ABSTRACT

A method and catalyst for producing an alcohol, which method includes supplying water and a C2-C5 olefin to a reactor and performing hydration in a gas phase using a solid acid catalyst. The solid acid catalyst is one in which a heteropolyacid or a salt thereof is supported on a silica carrier. The silica carrier is obtained by kneading a fumed silica obtained by a combustion method, a silica gel obtained by a gel method, and a colloidal silica obtained by a sol-gel method or a water glass method; molding the resulting kneaded product; and calcining the resulting molded body.

12 Claims, 2 Drawing Sheets

(51) Int. Cl.
*B01J 23/30* (2006.01)
*B01J 35/61* (2024.01)
*B01J 35/64* (2024.01)
*B01J 37/04* (2006.01)
*B01J 37/08* (2006.01)
*C07C 29/04* (2006.01)

(52) U.S. Cl.
CPC ........... *B01J 35/647* (2024.01); *B01J 35/651* (2024.01); *B01J 35/653* (2024.01); *B01J 37/04* (2013.01); *B01J 37/082* (2013.01); *C07C 29/04* (2013.01)

(58) Field of Classification Search
CPC ................ B01J 35/1061; B01J 35/1066; B01J 35/1071; B01J 37/04; B01J 35/647
See application file for complete search history.

(56) References Cited

U.S. PATENT DOCUMENTS

| | | | |
|---|---|---|---|
| 5,629,459 A | | 5/1997 | Atkins |
| 5,684,216 A | * | 11/1997 | Haining .................. B01J 21/08 |
| | | | 568/901 |
| 2020/0238255 A1 | | 7/2020 | Oguchi et al. |
| 2020/0239399 A1 | | 7/2020 | Itagaki et al. |

FOREIGN PATENT DOCUMENTS

| | | | | | |
|---|---|---|---|---|---|
| EP | 0 653 378 | A1 | 5/1995 | | |
| GB | 2 385 287 | A | 8/2003 | | |
| GB | 2385287 | * | 8/2003 | ............. | B01J 23/08 |
| GB | 2 398 749 | A | 9/2004 | | |
| JP | 8-192047 | A | 7/1996 | | |
| JP | 8-225473 | A | 9/1996 | | |
| JP | 10-101601 | A | 4/1998 | | |
| JP | 3041414 | B2 | 5/2000 | | |
| JP | 2002-145813 | A | 5/2002 | | |
| JP | 2003-190786 | A | 7/2003 | | |
| JP | 2004-148177 | A | 5/2004 | | |
| JP | 3901233 | B2 | 4/2007 | | |
| JP | 2008-088149 | A | 4/2008 | | |
| JP | 2008088149 | * | 4/2008 | ............. | C07C 45/52 |
| JP | 2019-42697 | A | 3/2019 | | |
| JP | 2019-043909 | A | 3/2019 | | |
| KR | 10-0413661 | B1 | 6/2004 | | |

OTHER PUBLICATIONS

Hiden Isochema, Glossary: Barrett-Joyner-Halenda (BJH) Analysis, abstract, 2 pages (Year: 2013).*
International Search Report for PCT/JP2019/042212, dated Jan. 21, 2020.

* cited by examiner

METHOD FOR PRODUCING ALCOHOL AND CATALYST FOR PRODUCING ALCOHOL

CROSS REFERENCE TO RELATED APPLICATIONS

This application is a National Stage of International Application No. PCT/JP2019/042212 filed Oct. 28, 2019, claiming priority based on Japanese Patent Application No. 2018-207344 filed Nov. 2, 2018.

FIELD

The present invention relates to a method for producing an alcohol by a hydration reaction of an olefin and a catalyst for producing an alcohol used in the reaction. The method for producing an alcohol and the catalyst for producing an alcohol described in the present disclosure are particularly suitable for producing ethanol from ethylene.

BACKGROUND

Industrial ethanol is an important industrial chemical product widely used as an organic solvent, an organic synthetic raw material, a disinfectant and an intermediate of chemicals. It is known that industrial ethanol can be obtained by a hydration reaction of ethylene in the presence of a liquid acid, such as sulfuric acid and sulfonic acid, a zeolite catalyst, a metal oxide catalyst including tungsten, niobium or tantalum, etc., a heteropolyacid, such as phosphotungstic acid and silicotungstic acid, or a solid catalyst in which phosphoric acid is supported on a silica carrier or a diatomite carrier. In the case of an ethylene hydration reaction in a liquid phase using a liquid acid, such as sulfuric acid and sulfonic acid, as a catalyst, a post-treatment of the acid used in the reaction is necessary. In addition, there are problems such as low activity, and limitations in industrial utilization. On the other hand, since the hydration reaction of ethylene using a solid acid catalyst supported by a carrier can be carried out in the form of a gas phase reaction, separation of a reactant and the catalyst is easy. In addition, there is an advantage that the reaction can be carried out in high temperature conditions which are advantageous in terms of reaction kinetics and in high pressure conditions which are advantageous in terms of the theory of equilibrium. Regarding solid acid catalysts, many proposals have been made so far, and in particular, a gas phase reaction process using a catalyst in which phosphoric acid is supported on a carrier has been industrially carried out. However, in an industrial process using a catalyst in which phosphoric acid is supported on a carrier, an efflux of phosphoric acid, which is an active component, continuously occurs, and as a result, the activity and selectivity decrease. Thus, continuous supply of phosphoric acid is required. There is also a problem that periodic maintenance of a reactor or other equipment is necessary, and thus this costs a lot to maintain them, since the effused phosphoric acid corrodes the equipment. Further, as a problem of the phosphorus acid supported catalyst, there may be a case where physical and chemical deterioration of the catalyst occurs due to contact with water vapor, and therefore, the activity decreases by use for a long period of time, and in the worse case scenario, carrier particles aggregate with each other into a block shape, so that replacement and extraction of the catalyst may be extremely difficult. Therefore, a novel carrier and a carrier-supported catalyst have been developed to solve these problems.

For example, Patent Literature 1 describes a hydration reaction of ethylene using a catalyst, in which titanium oxide is used as a carrier, and titanium oxide and tungsten oxide are used as essential components, to prevent phosphoric acid from flowing out. Patent Literature 2 describes a method for producing ethanol by a hydration reaction of ethylene using a catalyst, in which phosphoric acid is supported on a silica carrier having an average pore volume of at least 1.23 mL/g, which is superior in yield and selectivity to a conventional silica-supported phosphoric acid catalyst and is able to prevent a decrease in particle strength of the carrier. Patent Literature 3 describes a catalyst supported on a fumed silica obtained by combustion hydrolysis of a heteropolyacid, as a supported catalyst for a hydration reaction of an olefin having improved performance. Patent Literature 4 describes a catalyst in which a heteropolyacid is supported on a clay carrier treated with a heated acid, which is capable of improving the performance of a heteropolyacid-based catalyst. Patent Literature 5 describes a silica carrier having a specific pore volume, a specific surface area, and a pore diameter, as a carrier of a supported catalyst suitable for a hydration reaction of an olefin, and exemplifies an ethylene hydration catalyst in which a catalyst component is supported on the carrier.

CITATION LIST

Patent Literature

[PTL 1] JP 3041414 B
[PTL 2] JP H10-101601 A
[PTL 3] JP 3901233 B
[PTL 4] JP H8-225473 A
[PTL 5] JP 2003-190786 A

SUMMARY

Technical Problem

However, in any of these proposals, there is a problem that the hydration activity of ethylene is low, which is not sufficient for industrial use.

It is an object of the present invention to enhance the production efficiency of an alcohol by a hydration reaction of an olefin, and to provide a high performance catalyst used in the production of an alcohol by a hydration reaction of an olefin.

Solution to Problem

As a result of intensive studies, the present inventors have found that a silica carrier obtained by kneading a fumed silica obtained by a combustion method, a silica gel obtained by a gel method, and a colloidal silica obtained by a sol-gel method or a water glass method (ion exchange method), forming the obtained kneaded material, and then calcining the obtained shaped body is excellent as a carrier, since it has a large pore volume of macropores and a large BET specific surface area at the same time, and exhibits high activity in the production of an alcohol by a hydration reaction of an olefin when a heteropolyacid is supported thereon.

That is, the present invention includes the following [1] to [15].

[1]

A method for producing an alcohol comprising supplying water and an olefin having 2 to 5 carbon atoms to a reactor and subjecting them to a hydration reaction in a gas phase using a solid acid catalyst, the method characterized by using a solid acid catalyst in which a heteropolyacid or a salt thereof is supported on a silica carrier obtained by kneading a fumed silica obtained by a combustion method, a silica gel obtained by a gel method, and a colloidal silica obtained by a sol-gel method or a water glass method, forming the obtained kneaded material, and then calcining the obtained shaped body.

[2]

The method for producing an alcohol according to [1], wherein the blending amount of the fumed silica is 5 to 50 parts by mass, the blending amount of the silica gel is 40 to 90 parts by mass, and the blending amount of the solid content of the colloidal silica is 5 to 30 parts by mass.

[3]

The method for producing an alcohol according to [1] or [2], wherein the calcining temperature is 300 to 1000° C.

[4]

The method for producing an alcohol according to any one of [1] to [3], wherein the heteropolyacid is at least one compound selected from the group consisting of silicotungstic acid, phosphotungstic acid, phosphomolybdic acid, silicomolybdic acid, silicovanadotungstic acid, phosphovanadotungstic acid, and phosphovanadomolybdic acid.

[5]

A method for producing an alcohol comprising supplying water and an olefin having 2 to 5 carbon atoms to a reactor and subjecting them to a hydration reaction in a gas phase using a solid acid catalyst, the method characterized by using a solid acid catalyst in which a heteropolyacid or a salt thereof is supported on a silica carrier having mesopores having a pore diameter of 2 to 50 nm and macropores having a pore diameter of more than 50 nm and not more than 1000 nm in a pore diameter distribution measurement.

[6]

The method for producing an alcohol according to [5], wherein in the pore diameter distribution by the mercury intrusion method, the pore volume of the macropores of the silica carrier is 0.05 to 0.50 cc/g.

[7]

The method for producing an alcohol according to [5] or [6], wherein the BET specific surface area of the silica carrier is 200 to 500 $m^2/g$.

[8]

The method for producing an alcohol according to any one of [5] to [7], wherein the bulk density of the silica carrier is 300 to 750 g/L.

[9]

The method for producing an alcohol according to any one of [5] to [8], wherein the average pore diameter of the mesopores of the silica carrier by the BJH method is 3 to 16 nm.

[10]

The method for producing an alcohol according to any one of [5] to [9], wherein the particle diameter of the silica carrier is 0.5 to 12 mm.

[11]

The method for producing an alcohol according to any one of [5] to [10], wherein the heteropolyacid is at least one compound selected from the group consisting of silicotungstic acid, phosphotungstic acid, phosphomolybdic acid, silicomolybdic acid, silicovanadotungstic acid, phosphovanadotungstic acid, and phosphovanadomolybdic acid.

[12]

The method for producing an alcohol according to any one of [5] to [11], wherein the silica carrier is obtained by kneading a fumed silica obtained by a combustion method, a silica gel obtained by a gel method, and a colloidal silica obtained by a sol-gel method or a water glass method, forming the obtained kneaded material, and then calcining the obtained shaped body.

[13]

The method for producing an alcohol according to any one of [5] to [12], wherein the olefin having 2 to 5 carbon atoms is ethylene and the alcohol produced by the hydration reaction is ethanol.

[14]

The method for producing an alcohol according to [13], wherein an ether compound by-produced by the hydration reaction of ethylene is recycled into the reactor.

[15]

A catalyst for producing an alcohol by a hydration reaction of an olefin having 2 to 5 carbon atoms, characterized in that a heteropolyacid or a salt thereof is supported on a silica carrier having mesopores having a pore diameter of 2 to 50 nm and macropores having a pore diameter of more than 50 nm and not more than 1000 nm in a pore diameter distribution measurement.

Advantageous Effects of Invention

According to the production method described in the present disclosure, a highly active solid acid catalyst in which a heteropolyacid or a salt thereof is supported on a silica carrier having a specific structure is used for producing an alcohol by a hydration reaction of water and an olefin having 2 to 5 carbon atoms, for example, ethylene, so that production efficiency can be enhanced.

DESCRIPTION OF EMBODIMENTS

Figure 1:
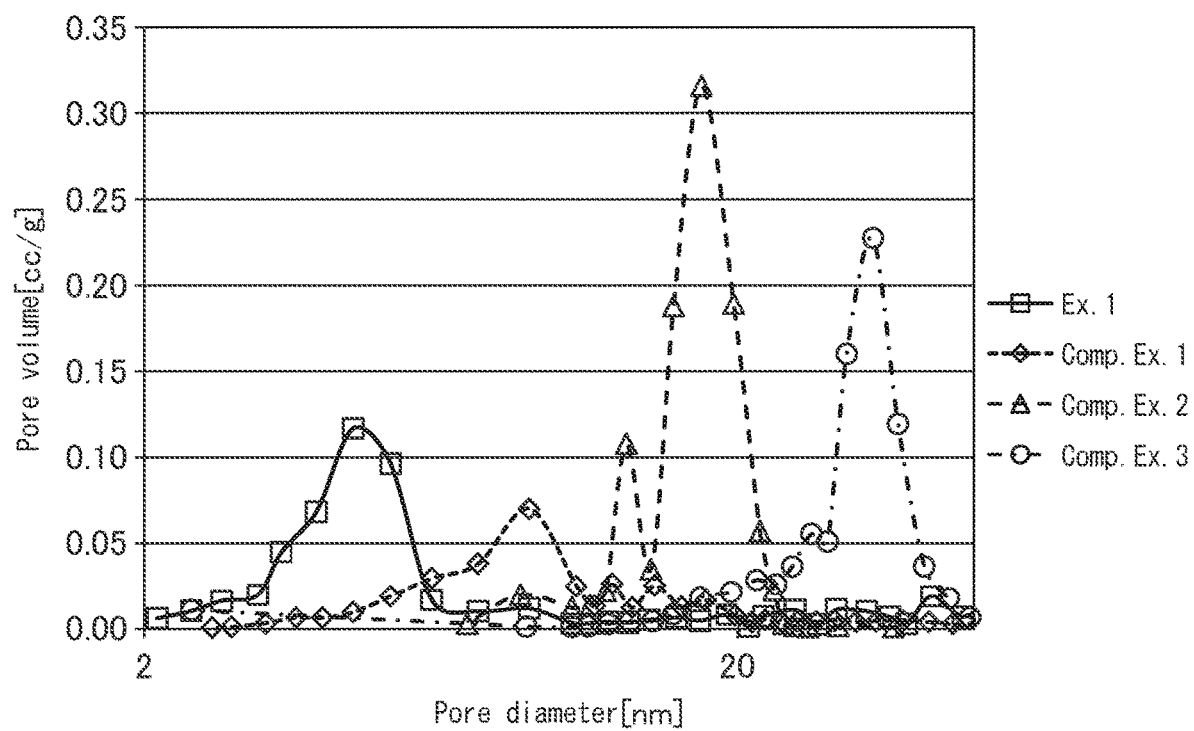
FIG. 1 A graph showing the pore diameter distribution of the silica carrier used in Example 1 and Comparative Examples 1 to 3 by the BJH method.

Hereinafter, preferred embodiments of the present invention will be described, but it should be understood that the present invention is not limited to these embodiments only, and various applications can be made within the spirit and practice of the present invention.

(Silica Carrier)

In general, synthetic amorphous silica is produced by either a dry method or a wet method. A combustion method in which silicon tetrachloride is combusted in a hydrogen flame in the presence of oxygen is classified into the dry method, while a gel method in which a neutralization reaction of sodium silicate and a mineral acid is allowed to proceed in an acidic pH region to cause aggregation in a state in which growth of primary particles is suppressed, a sol-gel method in which hydrolysis of an alkoxysilane is carried out, and a water glass method in which sodium silicate is ion-exchanged to prepare active silicic acid, and particles thereof are grown in an aqueous solution containing seed particles, the pH of which is adjusted under heating, are classified into the wet method. In general, a silica obtained by the combustion method is referred to as a fumed silica, a silica obtained by the gel method is referred to as a silica gel, a silica in which silica particles obtained by the sol-gel method or a water glass method are dispersed in a medium, such as water, is referred to as a colloidal silica, respectively.

A silica carrier according to one embodiment can be obtained by kneading a fumed silica obtained by the combustion method, a silica gel obtained by the gel method, and a colloidal silica obtained by the sol-gel method or the water glass method, forming the kneaded material, and then calcining the shaped body.

When the fumed silica, the silica gel, and the colloidal silica are kneaded and subjected to forming processing and calcined, the sizes of primary particles and secondary particles of the silica carrier after calcination, the internal state of a porous body, etc., may vary depending on the blending ratio of each component, the kneading method, the calcining conditions, etc., so that the higher order structure of the silica carrier of the present disclosure cannot be defined. The composition formula of the silica carrier is $SiO_2$.

There is no limitation on the fumed silica, and a general fumed silica can be used. Examples of a commercially available fumed silica include Aerosil™ manufactured by Nippon Aerosil Co., Ltd., Reolosil™ manufactured by Tokuyama Corporation, and CAB-O-SIL™ manufactured by Cabot Corporation. A commercially available fumed silica is a hydrophilic grade or a hydrophobic grade, both of which can be used. A typical fumed silica has physical properties, such as a primary particle diameter of 7 to 40 nm and a specific surface area of 50 to 500 $m^2/g$, is not porous without an inner surface area, is amorphous, has a purity as silicon oxide of 99% or more, and contains almost no metals and heavy metals.

There is no limitation on the silica gel, and a general silica gel can be used. Examples of a commercially available silica gel include NIPGEL manufactured by Tosoh Silica Corporation, MIZUKASIL manufactured by Mizusawa Industrial Chemicals, Ltd., CARiACT manufactured by Fuji Silysia Chemical Ltd., and SUNSPHERE manufactured by AGC Si-Tech Co., Ltd. In general, a silica gel is produced by using, as a raw material, sodium silicate in which sodium silicate glass (cullet) obtained by mixing and melting silica sand ($SiO_2$) and soda ash ($Na_2CO_3$) is dissolved in water, and carrying out a reaction between sodium silicate and a mineral acid, such as sulfuric acid, under acidic conditions to cause agglomeration while the growth of primary particles is suppressed, thereby gelling the entire reaction solution. Although there is no particular limitation on the physical properties of the silica gel, the silica gel has characteristics, such as small primary particles, high specific surface area, and hard secondary particles. Specific physical properties of the silica gel include a BET specific surface area of 200 to 1000 $m^2/g$ a secondary particle diameter of 1 to 30 micrometers, and a pore volume of 0.3 to 2.5 mL/g by a nitrogen gas adsorption method (BJH method). The higher the purity of the silica gel, the more preferable, and the preferred purity is 95% by mass or more, and more preferably 98% by mass or more.

There is also no particular limitation on the colloidal silica, and a general colloidal silica can be used. Examples of a commercially available colloidal silica include Snowtex™ manufactured by Nissan Chemical Corporation, Silicadol manufactured by Nippon Chemical Industrial Co., Ltd., Adelite manufactured by ADEKA Corporation, CAB-O-SIL™ TG-C colloidal silica manufactured by Cabot Corporation, and Quartron™ manufactured by Fuso Chemical Co., Ltd. A colloidal silica is obtained by dispersing silica fine particles in a medium, such as water. As a method for producing a colloidal silica, there are a water glass method and a sol-gel method by hydrolysis of an alkoxysilane, and a colloidal silica produced by either of the methods can be used. A colloidal silica produced by the water glass method and a colloidal silica produced by the sol-gel method may be used in combination. Typical physical properties of a colloidal silica include a particle diameter of 4 to 80 nm, and a solid concentration of 5 to 40% by mass of silica dispersed in water or an organic solvent. It is desirable that the impurity concentration in the colloidal silica be lower, since it may affect a catalytically active component to be supported. The silica purity in the solid content is preferably 99% by mass or more, and more preferably 99.5% by mass or more.

A silica carrier can be obtained by kneading the fumed silica, the silica gel, and the colloidal silica, forming the obtained kneaded material, and then calcining the shaped body. A suitable additive may be added during kneading. The blending ratio of the fumed silica, the silica gel, and the colloidal silica is preferably 5 to 50 parts by mass of the fumed silica, 40 to 90 parts by mass of the silica gel, and 5 to 30 parts by mass of the solid content of the colloidal silica. It is more preferable that the blending ratio be 15 to 40 parts by mass of the fumed silica, 45 to 75 parts by mass of the silica gel, and 5 to 15 parts by mass of the solid content of the colloidal silica.

When the fumed silica, the silica gel, and the colloidal silica are mixed, water or an additive may be added for the purpose of improving formability, increasing the strength of the resulting silica carrier, etc. The additive is not particularly limited, and an additive used in producing a general ceramic shaped body can be used. Depending on the purpose, a binder, a plasticizer, a dispersant, a lubricant, a wetting agent, a defoaming agent, etc., can be used.

Examples of the binder include a wax emulsion, gum arabic, a lignin, a dextrin, polyvinyl alcohol, polyethylene oxide, a starch, methylcellulose, Na-carboxymethylcellulose, hydroxyethylcellulose, sodium alginate, ammonium alginate, and tragacanth gum. Since the viscosity of the kneaded material varies greatly depending on the type and concentration of the binder, the type and amount of the binder are selected so that the kneaded material has a viscosity suitable for a forming method to be used.

Examples of the plasticizer include glycerin, polyethylene glycol, and dibutyl phthalate, so that the flexibility of the kneaded material can be increased.

Examples of the dispersant include, for an aqueous system, ammonium carboxymethylcellulose (CMC-$NH_4$), an oligomer of acrylic acid or its ammonium salt, an anionic surfactant, an ammonium polycarboxylate, a wax emulsion, amines, such as monoethylamine, pyridine, piperidine, and tetramethylammonium hydroxide, and for a nonaqueous system, a fatty acid, a fatty acid ester, a phosphate ester, a synthetic surfactant, and benzenesulfonic acid. By adding the dispersant to avoid the formation of aggregated particles, a silica carrier having a uniform fine structure can be obtained after calcination.

Examples of the lubricant include a hydrocarbon system, such as a liquid paraffin, a paraffin wax, and a chlorinated hydrocarbon, a fatty acid system, such as stearic acid, lauric acid and metal salts thereof, and a fatty acid amide system. By adding the lubricant, a friction between powders can be reduced, fluidity can be improved, forming can be facilitated, and extraction of a shaped body from a mold can be facilitated.

In order to improve the wetting characteristics of the powder and the dispersant, a wetting agent may be added. Examples of the wetting agent include, for an aqueous system, a nonionic surfactant, an alcohol, and a glycol, and for a nonaqueous system, polyethylene glycol ethyl ether, and a polyoxyethylene ester. These substances tend to be adsorbed at a solid-liquid interface, and the wetting of the solid is improved by lowering the interfacial tension.

When a slurry-like kneaded material is handled, a defoaming agent, such as a nonionic surfactant, a polyalkylene glycol-based derivative, and a polyether-based derivative, can also be added.

These additives can be used alone or in combination of a plurality thereof, and it is desirable that they be effective with as little addition as possible, be inexpensive, not react with the powder, be soluble in water or a solvent, decompose completely in an oxidizing or non-oxidizing atmosphere, for example, at a relatively low temperature of 400° C. or less, and not leave ash, in particular, alkali metals and heavy metals, after decomposition explosion, and a decomposed gas be not toxic and corrosive, and not interfere with the recycling of a debris which has not be used as a product.

The shape of the silica carrier is not particularly limited. Examples of the shape include a spherical shape, a cylindrical shape, a hollow cylindrical shape, a plate shape, an elliptical shape, a sheet shape, and a honeycomb shape. The shape is preferably spherical, cylindrical, hollow cylindrical, or elliptical, and more preferably spherical or cylindrical, in order to facilitate filling into the reactor and supporting of a catalytically active component.

A method for forming the silica carrier is not particularly limited. The silica carrier is formed from a kneaded material including the fumed silica, the silica gel, and the colloidal silica, by any suitable method, such as molding, extrusion, rolling granulation, and spray drying. A general molding involves placing the kneaded material in a metal mold, packing it sufficiently while striking it many times by using a hammer, etc., pressurizing it with a piston, and then removing it from the mold, and is also referred to as stamp forming. Extrusion generally involves packing the kneaded material into a press, extruding it from a die, cutting it so as to have an appropriate length, and forming it into a desired shape. Rolling granulation involves dropping the kneaded material onto a rotating disk placed tilted, and rolling grains on the disk to grow, and making them spherical. Spray drying generally does not produce large particles, and involves spraying a thick slurry into hot air to obtain porous particles.

The size of the silica carrier is not particularly limited. It is desirable that the size be determined by taking into consideration handling at the time of producing a catalyst which supports a catalytically active component or at the time of filling the catalyst, the differential pressure after filling it into a reactor, the reaction performance of the catalytic reaction, etc., since they are affected by the size. Since shrinkage of the carrier occurs during calcining the shaped body, the size of the silica carrier is determined by the calcining conditions. The size of the silica carrier (after calcining) in the case where the silica carrier is spherical is preferably 0.5 mm to 12 mm, more preferably 1 mm to 10 mm, and further preferably 2 mm to 8 mm in diameter. The size of the silica carrier (after calcining) in the case where the silica carrier is not spherical is preferably 0.5 mm to 12 mm, more preferably 1 mm to 10 mm, and further preferably 2 mm to 8 mm, in terms of a maximum dimensional length when the size is measured. When the particle diameter of the silica carrier is 0.5 mm or more, it is possible to prevent a decrease in productivity at the time of producing the carrier and an increase in pressure loss when used in the catalyst. When the particle diameter of the silica carrier is 12 mm or less, it is possible to prevent a decrease in reaction rate due to diffusion control within the carrier and an increase of by-products.

Before or after calcining, if necessary, the shape of the silica carrier can be adjusted by a treatment using Marumerizer (registered trademark) (Fuji Paudal Co., Ltd.), etc. For example, a cylindrical shaped body before calcination can be formed into a spherical shape by treating the cylindrical shaped body by using the aforementioned Marumerizer (registered trademark).

Although there is no particular limitation on the method for calcining, there is a suitable range of calcining temperatures from the viewpoint of decomposing the additive and preventing structural breakage of silica. The calcining temperature is preferably 300° C. to 1000° C., and more preferably 500° C. to 900° C. When the calcining temperature is within this range, the additive is completely decomposed and does not adversely affect the performance of the silica carrier. Further, the specific surface area of the silica carrier is also increased. Calcination can be carried out under oxidation or non-oxidation conditions. For example, calcination may be carried out under an air atmosphere, or may be carried out under an inert gas atmosphere, such as nitrogen gas. There is no particular limitation on the duration of calcination, which can be appropriately determined depending on the shape and size of the shaped body, the type and amount of the additive to be used, etc.

In one embodiment, the silica carrier has mesopores having a pore diameter of 2 to 50 nm and macropores having a pore diameter of more than 50 nm and not more than 1000 nm in a pore diameter distribution measurement. The presence of mesopores can be observed by a gas adsorption method (BJH method). The presence of macropores can be observed by a mercury intrusion method. In general, a mercury intrusion method and a gas adsorption method (BJH method) are widely used for pore diameter distribution measurement of porous materials, such as silica. According to the classification of pores in IUPAC (International Union of Pure and Applied Chemistry), macropores of 50 nm or more and a part of mesopores of 2 nm to less than 50 nm can be measured by the mercury intrusion method, and mesopores and micropores of 2 nm or less can be measured by the gas adsorption method. A silica carrier including macropores of the aforementioned size further improves the diffusion rate of a material in the pores. When such a silica carrier is used in a catalyst, an improvement in activity resulting from an increase of the main reaction rate, and an improvement in selectivity resulting from a suppression of sequential side reactions of the target product can be expected. A silica carrier including mesopores of the aforementioned size in combination with macropores, it is possible to highly disperse a supported component, and an improvement in catalytic activity resulting from an increase of reaction active sites.

In the silica carrier, the distribution ratio of each pore is not particularly limited, and an appropriate pore diameter distribution ratio can be selected depending on the type of reaction using the silica carrier. The pore diameter distribution ratio can be adjusted by a mixing ratio of the fumed silica, the silica gel, and the colloidal silica in the production of the silica carrier, a type and amount of an additive to be used, a calcining temperature, a forming method, etc.

In the pore diameter distribution by the mercury intrusion method, the pore volume of the macropores (integral of the total pore volume of macropores) of the silica carrier is preferably 0.05 to 0.50 cc/g. The pore volume of the macropores of the silica carrier is more preferably 0.07 to 0.40 cc/g, and further preferably 0.10 to 0.30 cc/g. When the pore volume of the macropores of the silica carrier is in the range of 0.05 to 0.50 cc/g, the diffusion rate of a material and the strength of the carrier are compatible with each other.

The specific surface area by the BET method (BET specific surface area) of the silica carrier is preferably 200 to 500 m$^2$/g. The BET specific surface area of the silica carrier is more preferably 220 to 400 m$^2$/g, and further preferably 240 to 400 m$^2$/g. When the BET specific surface area of the silica carrier is in the range of 200 to 500 m$^2$/g, a satisfactory reaction rate can be obtained when the silica carrier is used in a catalyst.

The bulk density of the silica carrier is preferably 300 to 750 g/L. The bulk density of the silica carrier is more preferably 350 to 700 g/L, and further preferably 450 to 600 g/L. When the bulk density of the silica carrier is in the range of 300 to 750 g/L, the required amount of active component can be supported and the strength of the carrier can be maintained.

The average pore diameter of the mesopores of the silica carrier by the gas adsorption method (BJH method) is preferably 3 to 16 nm. The average pore diameter of the mesopores of the silica carrier by the gas adsorption method (BJH method) is more preferably 4 to 14 nm, and further preferably 5 to 12 nm. When the average pore diameter of the mesopores of the silica carrier by the gas adsorption method (BJH method) is in the range of 3 to 16 nm, the specific surface area by the BET method is sufficient.

In the present disclosure, the pore diameter distribution by the gas adsorption method (BJH method), the pore diameter distribution by the mercury intrusion method, the BET specific surface area, the bulk density, and the average pore diameter of the mesopores by the BJH method are measured by the methods described in the Examples.

(Heteropolyacid and Heteropolyacid Salt)

A heteropolyacid is composed of a central element and a peripheral element to which oxygen is bonded. The central element is usually silicon or phosphorus, but may be any one selected from a wide variety of elements of Groups 1 to 17 of the Periodic Table of the Elements. Specific examples of the central element include a cupric ion; divalent ions of beryllium, zinc, cobalt and nickel; trivalent ions of boron, aluminum, gallium, iron, cerium, arsenic, antimony, phosphorus, bismuth, chromium and rhodium; tetravalent ions of silicon, germanium, tin, titanium, zirconium, vanadium, sulfur, tellurium, manganese, nickel, platinum, thorium, hafnium, cerium and other tetravalent rare earth ions; pentavalent ions of phosphorus, arsenic, vanadium, and antimony; a hexavalent ion of tellurium; and a heptavalent ion of iodine, but are not limited thereto. Specific examples of the peripheral element include tungsten, molybdenum, vanadium, niobium, and tantalum, but are not limited thereto.

Such heteropolyacids are also known as "polyoxoanions". "polyoxometalates" or "metal oxide clusters". The structures of some of the well known anions are named after the researchers in this field, and for example, the Keggin structure, the Wells-Dawson structure and the Anderson-Evans-Perloff structure are known. Details are described in "Chemistry of Polyacids" (edited by the Chemical Society of Japan, Quarterly Chemical Review No. 20, 1993). A heteropolyacid usually has a high molecular weight, e.g., a molecular weight in the range of 700 to 8500, and include not only a monomer thereof but also a dimeric complex thereof.

The salt of the heteropolyacid is not particularly limited as long as it is a metal salt or an onium salt in which some or all of the hydrogen atoms of the aforementioned heteropolyacid are substituted. Specific examples of the salt include metal salts of lithium, sodium, potassium, cesium, magnesium, barium, copper, gold and gallium, and onium salts of ammonia, etc., but are not limited thereto.

A heteropolyacid has relatively high solubility in polar solvents, such as water or other oxygenated solvents, particularly when the heteropolyacid is in the form of a free acid or some types of salts. The solubility of these salts can be controlled by selecting an appropriate counterion.

Examples of the heteropolyacid that can be used in the catalyst include:

silicotungstic acid: $H_4[SiW_{12}O_{40}] \cdot xH_2O$
phosphotungstic acid: $H_3[PW_{12}O_{40}] \cdot xH_2O$
phosphomolybdic acid: $H_3[PMo_{12}O_{40}] \cdot xH_2O$
silicomolybdic acid: $H_4[SiMo_{12}O_{40}] \cdot xH_2O$
silicovanadotungstic acid: $H_{4+n}[SiV_nW_{12-n}O_{40}] \cdot xH_2O$
phosphovanadotungstic acid: $H_{3+n}[PV_nW_{12-n}O_{40}] \cdot xH_2O$
phosphovanadomolybdic acid: $H_{3+n}[PV_nMo_{12-n}O_{40}] \cdot xH_2O$
silicovanadomolybdic acid: $H_{4+n}[SiV_nMo_{12-n}O_{40}] \cdot xH_2O$
silicomolybdotungstic acid: $H_4[SiMo_nW_{12-n}O_{40}] \cdot xH_2O$
phosphomolybdotungstic acid: $H_3[PMo_nW_{12-n}O_{40}] \cdot xH_2O$ wherein n is an integer of 1 to 11 and x is an integer greater than or equal to 1, but are not limited thereto.

The heteropolyacid is preferably silicotungstic acid, phosphotungstic acid, phosphomolybdic acid, silicomolybdic acid, silicovanadotungstic acid, phosphovanadotungstic acid, or phosphovanadomolybdic acid, and more preferably silicotungstic acid, phosphotungstic acid, silicovanadotungstic acid, or phosphovanadotungstic acid.

There is no particular limitation on the method for synthesizing such a heteropolyacid, and any methods may be used. For example, a heteropolyacid can be obtained by heating an acidic aqueous solution (approximately pH1 to pH2) containing a salt of molybdic acid or tungstic acid and a simple oxoacid of a heteroatom or a salt thereof. A heteropolyacid compound can be isolated, for example, by crystallization separation as a metal salt from the produced aqueous heteropolyacid solution. Specific examples of the manufacture of the heteropolyacid are described on page 1413 of "New Experimental Chemistry 8, Synthesis of Inorganic Compound (III)" (edited by the Chemical Society of Japan, published by Maruzen Co., Ltd., Aug. 20, 1984, third edition), but are not limited thereto. The structural confirmation of the synthesized heteropolyacid can be carried out by chemical analysis, as well as X-ray diffraction, UV, or IR measurements.

Preferred examples of the salt of the heteropolyacid include lithium salts, sodium salts, potassium salts, cesium salts, magnesium salts, barium salts, copper salts, gold salts, gallium salts, and ammonium salts of the aforementioned preferred heteropolyacids.

Specific examples of the salt of the heteropolyacid include a lithium salt of silicotungstic acid, a sodium salt of silicotungstic acid, a cesium salt of silicotungstic acid, a copper salt of silicotungstic acid, a gold salt of silicotungstic acid, a gallium salt of silicotungstic acid; a lithium salt of phosphotungstic acid, a sodium salt of phosphotungstic acid, a cesium salt of phosphotungstic acid, a copper salt of phosphotungstic acid, a gold salt of phosphotungstic acid, a gallium salt of phosphotungstic acid; a lithium salt of phosphomolybdic acid, a sodium salt of phosphomolybdic acid, a cesium salt of phosphomolybdic acid, a copper salt of phosphomolybdic acid, a gold salt of phosphomolybdic acid, a gallium salt of phosphomolybdic acid; a lithium salt of silicomolybdic acid, a sodium salt of silicomolybdic acid, a cesium salt of silicomolybdic acid, a copper salt of silicomolybdic acid, a gold salt of silicomolybdic acid, a gallium salt of silicomolybdic acid; a lithium salt of silicovanadotungstic acid, a sodium salt of silicovanadotungstic acid, a cesium salt of silicovanadotungstic acid, a copper salt of silicovanadotungstic acid, a gold salt of silicovanadotungstic acid, a gallium salt of silicovanadotungstic acid; a lithium salt of phosphovanadotungstic acid, a sodium salt of phosphovanadotungstic acid, a cesium salt of phosphovanadotungstic acid, a copper salt of phosphovanadotungstic acid, a gold salt of phosphovanadotungstic acid, a gallium salt of phosphovanadotungstic acid; a lithium salt of phosphovanadomolybdic acid, a sodium salt of phosphovanadomolybdic acid, a cesium salt of phosphovanadomolybdic acid, a copper salt of phosphovanadomolybdic acid, a gold salt of phosphovanadomolybdic acid, a gallium salt of phosphovanadomolybdic acid; a lithium salt of silicovanadomolybdic acid, a sodium salt of silicovanadomolybdic acid, a cesium salt of silicovanadomolybdic acid, a copper salt of silicovanadomolybdic acid, a gold salt of silicovanadomolybdic acid, and a gallium salt of silicovanadomolybdic acid.

The salt of the heteropolyacid is preferably a lithium salt of silicotungstic acid, a sodium salt of silicotungstic acid, a cesium salt of silicotungstic acid, a copper salt of silicotungstic acid, a gold salt of silicotungstic acid, a gallium salt of silicotungstic acid; a lithium salt of phosphotungstic acid, a sodium salt of phosphotungstic acid, a cesium salt of phosphotungstic acid, a copper salt of phosphotungstic acid, a gold salt of phosphotungstic acid, a gallium salt of phosphotungstic acid; a lithium salt of phosphomolybdic acid, a sodium salt of phosphomolybdic acid, a cesium salt of phosphomolybdic acid, a copper salt of phosphomolybdic acid, a gold salt of phosphomolybdic acid, a gallium salt of phosphomolybdic acid; a lithium salt of silicomolybdic acid, a sodium salt of silicomolybdic acid, a cesium salt of silicomolybdic acid, a copper salt of silicomolybdic acid, a gold salt of silicomolybdic acid, a gallium salt of silicomolybdic acid; a lithium salt of silicovanadotungstic acid, a sodium salt of silicovanadotungstic acid, a cesium salt of silicovanadotungstic acid, a copper salt of silicovanadotungstic acid, a gold salt of silicovanadotungstic acid, a gallium salt of silicovanadotungstic acid; a lithium salt of phosphovanadotungstic acid, a sodium salt of phosphovanadotungstic acid, a cesium salt of phosphovanadotungstic acid, a copper salt of phosphovanadotungstic acid, a gold salt of phosphovanadotungstic acid, a gallium salt of phosphovanadotungstic acid; a lithium salt of phosphovanadomolybdic acid, a sodium salt of phosphovanadomolybdic acid, a cesium salt of phosphovanadomolybdic acid, a copper salt of phosphovanadomolybdic acid, a gold salt of phosphovanadomolybdic acid, a gallium salt of phosphovanadomolybdic acid; a lithium salt of silicovanadomolybdic acid, or a sodium salt of silicovanadomolybdic acid.

The salt of the heteropolyacid is more preferably a lithium salt of silicotungstic acid, a sodium salt of silicotungstic acid, a cesium salt of silicotungstic acid, a copper salt of silicotungstic acid, a gold salt of silicotungstic acid, a gallium salt of silicotungstic acid; a lithium salt of phosphotungstic acid, a sodium salt of phosphotungstic acid, a cesium salt of phosphotungstic acid, a copper salt of phosphotungstic acid, a gold salt of phosphotungstic acid, a gallium salt of phosphotungstic acid; a lithium salt of silicovanadotungstic acid, a sodium salt of silicovanadotungstic acid, a cesium salt of silicovanadotungstic acid, a copper salt of silicovanadotungstic acid, a gold salt of silicovanadotungstic acid, a gallium salt of silicovanadotungstic acid; a lithium salt of phosphovanadotungstic acid, a sodium salt of phosphovanadotungstic acid, a cesium salt of phosphovanadotungstic acid, a copper salt of phosphovanadotungstic acid, a gold salt of phosphovanadotungstic acid, or a gallium salt of phosphovanadotungstic acid.

As the salt of the heteropolyacid, it is particularly preferable that a lithium salt of silicotungstic acid or a cesium salt of phosphotungstic acid be used.

The aforementioned silica carrier is used as a carrier.

The carrier may be of any shape, and there is no particular limitation on its shape. The carrier may be, for example, powdery, spherical, or pelletized, and is preferably spherical or pelletized. There is no particular limitation on the particle diameter of the carrier. The particle diameter of the carrier varies depending on the mode of reaction, and is preferably 2 mm to 10 mm, and more preferably 3 mm to 7 mm, when used in a fixed bed system.

There is no particular limitation on the method for supporting the heteropolyacid or the salt thereof on the carrier. In general, it can be carried out by making the carrier absorb a solution or suspension obtained by dissolving or suspending the heteropolyacid or the salt thereof in a solvent and evaporating the solvent.

Examples of the method for supporting the salt of the heteropolyacid on the carrier include a method including supporting a raw material of an element for forming the salt after supporting the heteropolyacid on the carrier, a method including supporting the heteropolyacid and a raw material of an element for forming the salt together on the carrier, a method including supporting the salt of the heteropolyacid prepared in advance on the carrier, and a method including supporting the heteropolyacid after supporting a raw material of an element for forming the salt on the carrier, but are not limited thereto. In any of the above methods, the heteropolyacid, the salt thereof, and the raw material of an element forming the salt can be dissolved or suspended in a suitable solvent and supported on the carrier. The solvent may be any solvent capable of dissolving or suspending the heteropolyacid, the salt thereof, or the raw material of an element forming the salt, and water, an organic solvent, or a mixture thereof, is used, and water, an alcohol, or a mixture thereof is preferably used.

The amount of the heteropolyacid or the salt thereof to be supported on the carrier can be adjusted, for example, by dissolving the heteropolyacid or the salt thereof in an amount of distilled water that corresponds to the amount of water absorbed by the carrier, and impregnating the carrier with the solution. In another embodiment, the amount of the heteropolyacid or the salt thereof to be supported on the carrier can also be adjusted by immersing the carrier in a solution of an excess amount of the heteropolyacid or the salt thereof with moderate movement, followed by filtration to remove excess heteropolyacid or a salt thereof. The volume of the solution or suspension varies depending on the carrier used, the supporting method, etc. By placing a carrier in which the heteropolyacid or the salt thereof is impregnated in a heating oven for several hours to evaporate a solvent, a solid acid catalyst supported on the carrier can be obtained. The drying method is not particularly limited, and various methods, such as a stationary method, and a belt conveyor method, can be used. The amount of the heteropolyacid or the salt thereof supported on the carrier can be accurately measured by chemical analysis, such as ICP and XRF.

The amount of the heteropolyacid or the salt thereof supported on the carrier is preferably 10 to 150 parts by mass, and more preferably 30 to 100 parts by mass, in terms of the total mass of the heteropolyacid and the salt thereof with respect to 100 parts by mass of the carrier.

(Method for Producing Alcohol by Hydration Reaction of Olefin)

An alcohol can be obtained by supplying water and an olefin having 2 to 5 carbon atoms to a reactor and subjecting them to a hydration reaction in a gas phase, using a solid acid catalyst for producing an alcohol on which the heteropolyacid or the salt of the heteropolyacid is supported on the silica carrier specified by the present disclosure (hereinafter, simply referred to as a "catalyst for producing an alcohol" in the present disclosure).

A specific example of the alcohol production reaction by the hydration reaction of an olefin having 2 to 5 carbon atoms is represented by Formula (1):

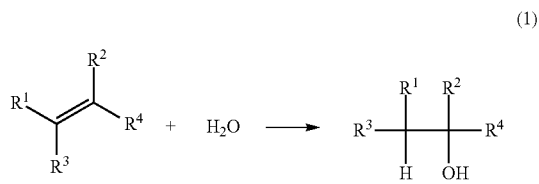

(1)

wherein $R^1$ to $R^4$ each independently represent a hydrogen atom or an alkyl group having 1 to 3 carbon atoms, and the sum of the carbon atoms of $R^1$ to $R^4$ is 0 to 3.

There is no particular limitation on the olefin having 2 to 5 carbon atoms which can be used in the hydration reaction of an olefin using the catalyst for producing an alcohol. The olefin having 2 to 5 carbon atoms is preferably ethylene, propylene, n-butene, isobutene, pentene or a mixture of two or more thereof, and more preferably ethylene. There is no limitation on the use ratio of the olefin and water; however, since the concentration dependence of the olefin on the reaction rate is large and the energy cost of the alcohol production process increases when the water concentration is high, the molar ratio of the olefin to water is preferably water/olefin=0.01 to 2.0, and more preferably water/olefin=0.1 to 1.0.

There is no limitation on the mode of the hydration reaction of an olefin using the catalyst for producing an alcohol, and any of the reaction modes can be used. From the viewpoint of ease of separation from the catalyst and reaction efficiency, the preferred examples of the mode include a fixed-bed, a fluidized-bed, and a suspension-bed, and more preferably a fixed-bed that requires the least energy for separation from the catalyst.

The gas space velocity in the case of using a fixed-bed is not particularly limited, but is preferably 500 to 15,000/hr, and more preferably 1000 to 10,000/hr, from the viewpoint of energy and reaction efficiency. When the gas space velocity is 500/hr or more, the amount of the catalyst used can be effectively reduced, and when the gas space velocity is 15000/hr or less, the amount of gas circulation can be reduced, so that the production of alcohol can be more efficiently carried out within the above ranges.

There is no limitation on the reaction pressure in the hydration reaction of an olefin using the catalyst for producing an alcohol. Since the hydration reaction of an olefin is a reaction in which the number of molecules decreases, it is generally advantageous to proceed at high pressure. The reaction pressure is preferably 0.5 to 7.0 MPaG, and more preferably 1.5 to 4.0 MPaG. "G" means a gauge pressure. When the reaction pressure is 0.5 MPaG or more, a satisfactory reaction rate can be obtained, and when the reaction pressure is 7.0 MPaG or less, it is possible to further reduce costs regarding installation of equipment as countermeasures for condensation of an olefin and in relation to evaporation of an olefin, equipment for high pressure gas safety, and energy.

The reaction temperature of the hydration reaction of an olefin using the catalyst for producing an alcohol is not particularly limited, and the reaction can be carried out at a wide range of temperatures. In view of the thermal stability of the heteropolyacid or the salt of the heteropolyacid and the temperature at which water, one of the raw materials, does not condense, the preferred reaction temperature is 100 to 550° C., and more preferably 150 to 350° C.

The hydration reaction of an olefin using the catalyst for producing an alcohol is an equilibrium reaction, and the conversion rate of olefin will be an equilibrium conversion rate at most. For example, the equilibrium conversion rate in the production of ethanol by the hydration of ethylene is calculated to be 7.5% at a temperature of 200° C. and a pressure of 2.0 MPaG. Therefore, in the method for producing an alcohol by the hydration of an olefin, a maximum conversion rate is determined by the equilibrium conversion rate, and as can be seen in an example of ethylene, the hydration reaction of an olefin tends to have a small equilibrium conversion rate, and therefore it is strongly required in the industry to carry out the hydration reaction of an olefin with high efficiency under mild conditions.

In the hydration reaction of an olefin using the catalyst for producing an alcohol, loss of the olefin can be reduced by recycling any unreacted olefin into a reactor. There is no limitation on the method for recycling the unreacted olefin into the reactor, and the olefin may be isolated and recycled from a process fluid coming out of the reactor, or may be recycled together with other inert components. Typically, industrial grade ethylene often contains a very small amount of ethane. Therefore, when ethylene containing ethane is used and the unreacted ethylene is recycled to the reactor, it is desirable to purge a portion of the recovered ethylene gas out of the system, in order to prevent concentration and accumulation of ethane.

In the hydration reaction of an olefin using the catalyst for producing an alcohol, the produced alcohol may be dehydrated to generate an ether compound as a by-product. For example, when ethanol is obtained by the hydration of ethylene, diethyl ether is by-produced. It is considered that this diethyl ether is generated by a dehydration reaction of two molecules of ethanol, and when ethanol is produced by the hydration reaction of ethylene, the reaction yield is remarkably lowered. However, by recycling the by-produced diethyl ether into the reactor, diethyl ether is converted into ethanol, so that ethanol can be produced from ethylene with extremely high efficiency. Although there is no particular limitation on the method for recycling the by-produced ether compound into the reactor, there are, for example, a method including isolating an ether compound from components distilled from the reactor and recycling the ether compound into the reactor, and a method including recycling the ether compound into the reactor as a gas component together with an unreacted olefin.

EXAMPLES

Although the present invention will be further described with reference to the following Examples and Comparative Examples, these examples illustrate the summary of the present invention, and the present invention is not limited to these examples.

1. Preparation of Silica Carrier

A fumed silica, a silica gel, and a colloidal silica, and optionally water and/or additives were placed in a kneader and kneaded to prepare a kneaded material. Next, the kneaded material was put into an extruder, to which a die having a circular hole of a desired size at a tip thereof was attached. Next, a cylindrical shaped body before calcination was obtained by cutting an intermediate material extruded from the extruder to a desired size with a cutter. After the shaped body before calcination was subjected to a process with Marumerizer (registered trademark), preliminary drying was carried out, and then a calcining treatment was carried out at a temperature of 700° C. to 900° C. under an air atmosphere to obtain a silica carrier. Detailed conditions are described in each production example.

The water absorption rate of the carrier refers to a numerical value measured by the following measurement method.

(1) Weigh about 5 g of the carrier on a balance (W1 g), and place the carrier in a 100 mL beaker.
(2) Add about 15 mL of pure water (ion-exchanged water) to the beaker so as to completely cover the carrier.
(3) Allow the carrier to stand for 30 minutes.
(4) Drain pure water by putting the carrier and pure water on a wire mesh.
(5) Remove water adhering to the surface of the carrier by lightly pressing with a paper towel until there is no gloss on the surface.
(6) Measure the mass of the carrier and pure water (W2 g).
(7) Calculate a water absorption rate of the carrier by the following formula.

Water absorption rate (water (g)/carrier (g))=$(W2-W1)/W1$

Therefore, the water absorption amount (g) of the carrier is calculated by the water absorption rate (g/g) of the carrier×the mass of the carrier used (g).

2. Bulk Density Measurement of Silica Carrier

A silica carrier was put into a tared glass graduated cylinder in several parts, and the graduated cylinder containing the carrier or a catalyst (in which a catalyst metal, etc., is supported on the carrier) was tapped every time the silica carrier was put into the graduated cylinder, so that the carrier was put into the graduated cylinder until it reached a measurement volume of the graduated cylinder. Then, the mass of the graduated cylinder containing the carrier was measured, and the bulk density of the carrier was determined based on the tare and volume of the graduated cylinder.

3. BET Specific Surface Area Measurement of Silica Carrier and Catalyst for Producing Alcohol Using a gas adsorption apparatus (ASAP 2020) manufactured by Shimadzu Corporation, a BET specific surface area based on nitrogen gas adsorption of a silica carrier or a catalyst was measured. Further, the pore diameter distribution of the silica carrier by the BJH method was measured, and the average pore diameter of the mesopores was measured.

4. Measurement of Pore Diameter Distribution of Silica Carrier by Mercury Intrusion Method The pore diameter distribution of a silica carrier was measured by the mercury intrusion method using AutoPore IV 9500 manufactured by Shimadzu Corporation. In the pore diameter distribution, the pore volume (cc/g) of a peak derived from the macropores among pores of 30 to 300 nm was measured.

5. Raw Material Silica

Raw material silicas used are shown in Table 1.

TABLE 1

|  | Number | Specific surface area ($m^2$/g) | Average pore diameter (nm) | Average particle diameter (μm) | Purity (%) |
| --- | --- | --- | --- | --- | --- |
| Fumed silica | F-1 | 380 | No pores | 0.007 | 99.9 |
|  | F-2 | 200 | No pores | 0.012 | 99.9 |
| Silica gel | S-1 | 500 | 6 | 5 | 99.9 |
|  | S-2 | 360 | 8 | 5 | 99.9 |
|  | S-3 | 300 | 10 | 5 | 99.9 |
|  | S-4 | 850 | 5 | 5 | 99.9 |
| Colloidal silica | C-1 | — | — | 0.012 | — |

★ Colloidal silica: solid content: 20% by mass

6. Preparation of Catalyst for Producing Alcohol in which Heteropolyacid is Supported on Silica Carrier A desired amount of heteropolyacid was weighed, and put into a graduated cylinder, and distilled water was added to a mass corresponding to 95% of the water absorption amount of a silica carrier, and the heteropolyacid was dissolved or suspended and then transferred into a volumetric flask. A silica carrier was then weighed in a desired amount and put into the volumetric flask containing the solution or suspension of the heteropolyacid. After putting the silica carrier, the volumetric flask was stirred for a certain period of time, so that the liquid was in contact with the silica carrier to make the heteropolyacid supported thereon. A catalyst supporting thereon the heteropolyacid was removed from the volumetric flask, spread on a tray, and air-dried for several hours. Then, the air-dried silica carrier on which the heteropolyacid was supported was placed in a dryer with being kept on the tray, and dried under a condition of 130° C. for 5 hours, and then removed from the dryer, transferred into a dried desiccator, and cooled to room temperature, to obtain a catalyst for producing an alcohol in which the heteropolyacid was supported on the silica carrier.

7. Preparation of Catalyst for Producing Alcohol in which Salt of Heteropolyacid is Supported on Silica Carrier A desired amount of heteropolyacid and a metal salt were weighed, and put into a graduated cylinder, and distilled water was added to a mass corresponding to 95% of the water absorption amount of a silica carrier, and the heteropolyacid and the metal salt were dissolved or suspended and then transferred into a volumetric flask. A silica carrier was then weighed in a desired amount and put into the volumetric flask containing the solution or suspension of the heteropolyacid and the metal salt. After putting the silica carrier, the volumetric flask was stirred for a certain period of time, so that the liquid was in contact with the silica carrier to make the salt of the heteropolyacid supported thereon. A catalyst supporting thereon the salt of the heteropolyacid was removed from the volumetric flask, spread on a tray, and air-dried for several hours. Then, the air-dried silica carrier on which the salt of the heteropolyacid was supported was placed in a dryer with being kept on the tray, and dried under a condition of 130° C. for 5 hours, and then removed from the dryer, transferred into a dried desiccator, and cooled to room temperature, to obtain a catalyst for producing an alcohol in which the salt of the heteropolyacid was supported on the silica carrier.

8. Hydration Reaction of Olefin (One-Pass Evaluation)

A reactor filled with a predetermined amount of the catalyst for producing an alcohol was controlled to reach a predetermined temperature and to be pressurized to a predetermined pressure, and a predetermined amount of water vaporized by an evaporator and a predetermined amount of ethylene from a mass flow controller were introduced into the reactor. A reaction gas after passing through the reactor was cooled, and a condensed liquid and the reaction gas from which the condensate was removed were sampled for a certain period of time, respectively. The sampled liquid (reaction liquid) and the reaction gas were analyzed using a gas chromatography analyzer and a Karl Fischer analyzer to calculate the reaction results.

9. Hydration Reaction of Olefin (Gas Recycling Evaluation)

A reactor filled with a predetermined amount of the catalyst for producing an alcohol was controlled to reach a predetermined temperature and to be pressurized to a predetermined pressure, and a predetermined amount of water vaporized by an evaporator and a predetermined amount of ethylene from a mass flow controller were introduced into the reactor. A reaction gas after passing through the reactor was cooled, and a condensed liquid and the reaction gas from which the condensate was removed were sampled for a certain period of time, respectively. The reaction gas from which the condensate was removed was partially purged, so that an inert gas, such as ethane, did not accumulate, and the remaining gas was introduced into a compressor as a recycling gas and increased in pressure to be recycled into the reactor. The sampled liquid (reaction liquid) and the reaction gas were analyzed using a gas chromatography analyzer and a Karl Fischer analyzer to calculate the reaction results.

10. Analysis of Reaction Gas

The sampled reaction gas was analyzed by using a gas chromatography apparatus (apparatus name: 7890) manufactured by Agilent Technologies Japan, Ltd., and a system program based on a plurality of columns and two detectors.

Gas chromatography conditions:
  Oven: kept at 40° C. for 3 minutes, then raised to 200° C. at 20° C./min
  Carrier gas: helium
  Split ratio: 10:1
Columns used: manufactured by Agilent Technologies Japan. Ltd.
  HP-1 (2 m)+GasPro (30 m) 32 m×320 μm×0 μm
  DB-624: 60 m×320 μm×1.8 μm
Detectors:
  Front detector: FID (heater: 230° C., hydrogen flow rate 40 mL/min, air flow rate 400 L/min)
  Back detector: FID (heater: 230° C., hydrogen flow rate 40 mL/min, air flow rate 400 L/min)
  Aux detector: TCD (heater: 230° C., reference flow rate 45 mL/min, make-up flow rate 2 mL/min)

11. Analysis of Reaction Solution

The sampled reaction solution was analyzed by using a gas chromatography apparatus (apparatus name: 6850) manufactured by Agilent Technologies Japan, Ltd. Further, the concentration of water in the reaction solution was analyzed by a Karl Fischer analyzer manufactured by Mitsubishi Chemical Co., Ltd.

Columns used: PoraBONDQ 25 m×0.53 mm ID×10 μM
  Oven temperature: kept at 100° C. for 2 minutes, then raised to 240° C. at 5° C./min.
  Injection temperature: 250° C.
  Detector temperature: 300° C.

Preparation Example 1

Figure 2:
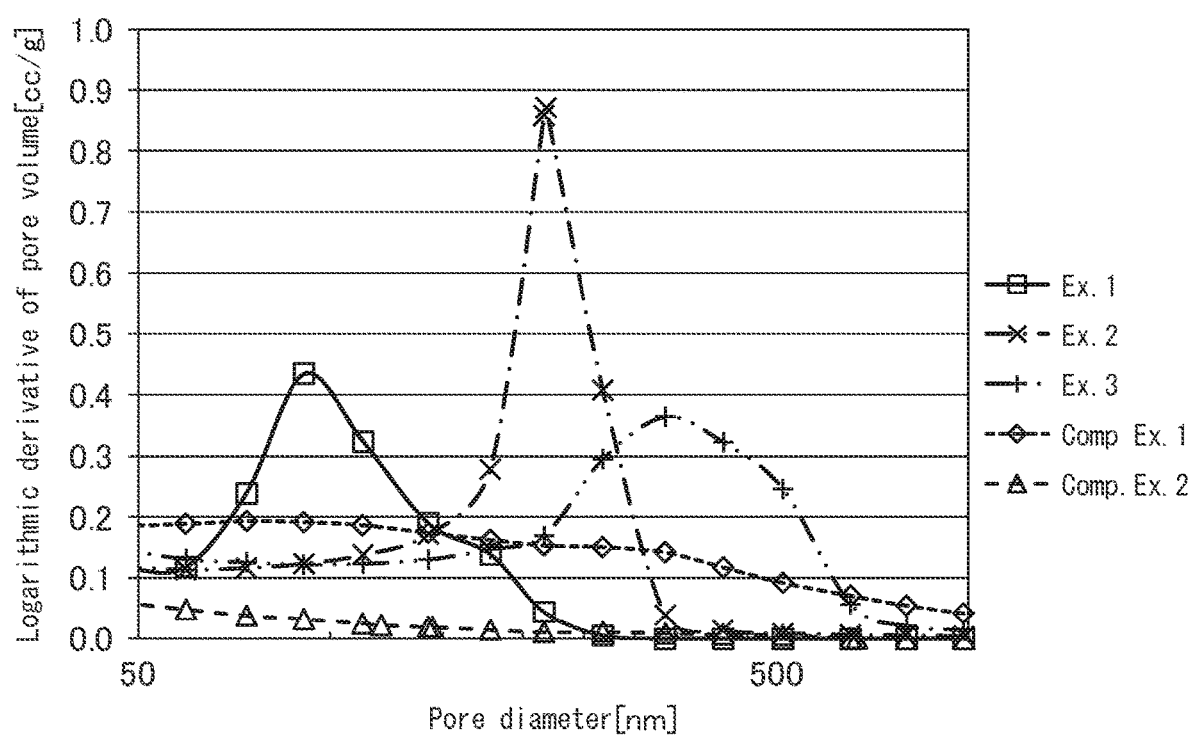
FIG. 2 A graph showing the pore diameter distribution of the silica carrier used in Examples 1 to 3 and Comparative Examples 1 to 2 by the mercury intrusion method.

25 parts by mass of fumed silica F-1, 75 parts by mass of silica gel S-1, and 45 parts by mass of colloidal silica C-1 (9 parts by mass in terms of solid content) were kneaded by a kneader, and then water and additives (10 parts by mass of methyl cellulose: SM-4000 manufactured by Shin-Etsu Chemical Co., Ltd., and 5 parts by mass of a resin-based binder: Cerander (registered trademark) YB-132A manufactured by Yuken Industry Co., Ltd.) were added in an appropriate amount, with the status of a mixture being monitored, and the mixture was further kneaded to obtain a kneaded material. Next, the kneaded material was put into an extruder, to which a die having a circular hole of 6 mmφ was attached, the kneaded material was extruded, and the extruded intermediate material was subjected to extrusion molding while cutting with a cutter so that the extruded intermediate material had the same length as the diameter of the circular hole used. The obtained shaped body before calcination was formed into a spherical shape by Marumerizer (registered trademark), and then dried at 70° C. for 24 hours or more, and calcined at about 820° C. under an air atmosphere, and cooled to obtain a silica carrier A. Table 2 shows measurement results of the BET specific surface area, BJH method average pore diameter, bulk density, etc., of the obtained silica carrier A. The pore diameter distribution of the silica carrier A by the BJH method is shown in FIG. 1 as Example 1, and a measurement result of the pore diameter distribution by the mercury intrusion method is shown in FIG. 2 as Example 1.

Preparation Examples 2 to 11

Silica carriers B to K were obtained in the same manner as in Production Example 1, except that the types and amounts of a fumed silica, a silica gel, and a colloidal silica, and the calcining temperature were as described in Table 2. However, in Production Examples 4 to 11, a die having a circular hole of 3 mmφ was used. Table 2 shows measurement results of the BET specific surface areas, BJH method average pore diameters, bulk densities, etc., of the obtained silica carriers. Further, measurement results of the pore diameter distribution by the mercury intrusion method of the silica carriers B and C are shown in FIG. 2 as Example 2 and Example 3, respectively.

Comparative Production Example 1

An attempt was made to produce silica carrier L of Comparative Production Example 1 in the same manner as in Production Example 1, except that colloidal silica was not used, but a shaped body usable as a carrier could not be obtained.

Comparative Production Example 2

An attempt was made to produce silica carrier M of Comparative Production Example 2 in the same manner as in Production Example 1, except that fumed silica was not used, but a shaped body usable as a carrier could not be obtained.

Comparative Production Example 3

An attempt was made to produce silica carrier N of Comparative Production Example 3 in the same manner as in Production Example 1, except that silica gel was not used, but a shaped body usable as a carrier could not be obtained.

Comparative Carrier Example 4

Table 3 shows measurement results of the BET specific surface area, BJH method average pore diameter, bulk density, etc., of KA-160 (silica carrier P), a silica carrier manufactured by Clariant Catalysts K.K., which is a commercially available silica gel derived from a natural product. The pore diameter distribution of the silica carrier P by the BJH method is shown in FIG. 1 as Comparative Example 1, and a measurement result of the pore diameter distribution by the mercury intrusion method is shown in FIG. 2 as Comparative Example 1.

Comparative Carrier Example 5

Table 3 shows measurement results of the BET specific surface area, BJH method average pore diameter, bulk density, etc., of CARiACT Q-15 (silica carrier Q), a silica carrier manufactured by Fuji Silysia Chemical Ltd., which is a commercially available silica gel. The pore diameter distribution of the silica carrier Q by the BJH method is shown in FIG. 1 as Comparative Example 2, and a measurement result of the pore diameter distribution by the mercury intrusion method is shown in FIG. 2 as Comparative Example 2.

Comparative Carrier Example 6

Table 3 shows measurement results of the BET specific surface area. BJH method average pore diameter, bulk density, etc., of CARiACT Q-30 (silica carrier R), a silica carrier manufactured by Fuji Silysia Chemical Ltd., which is a commercially available silica gel. A measurement result of the pore diameter distribution of the silica carrier R by the BJH method is shown in FIG. 1 as Comparative Example 3.

Comparative Carrier Example 7

Table 3 shows measurement results of the BET specific surface area, BJH method average pore diameter, bulk density, etc., of CARiACT Q-6 (silica carrier S), a silica carrier manufactured by Fuji Silysia Chemical Ltd., which is a commercially available silica gel.

TABLE 2

| Silica carrier | Particle diameter (mm) | Fumed silica | | | Silica get | | | Colloidal silica Blending amount (solid content) | | | Calcining temp. (° C.) |
|---|---|---|---|---|---|---|---|---|---|---|---|
| | | Type | Parts by mass | Mass % | Type | Parts by mass | Mass % | Type | Parts by mass | Mass % | |
| Carrier A | 6 | F-1 | 25 | 22.9 | S-1 | 75 | 68.8 | C-1 | 9 | 8.3 | 820 |
| Carrier B | 6 | F-1 | 25 | 22.9 | S-2 | 75 | 68.8 | C-1 | 9 | 8.3 | 820 |
| Carrier C | 6 | F-1 | 25 | 22.9 | S-3 | 75 | 68.8 | C-1 | 9 | 8.3 | 820 |
| Carrier D | 3 | F-1 | 25 | 22.9 | S-2 | 75 | 68.8 | C-1 | 9 | 8.3 | 820 |
| Carrier E | 3 | F-1 | 25 | 22.9 | S-1 | 75 | 68.8 | C-1 | 9 | 8.3 | 820 |
| Carrier F | 3 | F-1 | 10 | 9.2 | S-1 | 90 | 82.6 | C-1 | 9 | 8.3 | 820 |
| Carrier G | 3 | F-1 | 40 | 36.7 | S-1 | 60 | 55.0 | C-1 | 9 | 8.3 | 820 |
| Carrier H | 3 | F-2 | 25 | 22.9 | S-1 | 75 | 68.8 | C-1 | 9 | 8.3 | 820 |
| Carrier I | 3 | F-1 | 25 | 22.9 | S-1 | 75 | 68.8 | C-1 | 9 | 8.3 | 750 |
| Carrier J | 3 | F-1 | 25 | 22.9 | S-1 | 75 | 68.8 | C-1 | 9 | 8.3 | 700 |
| Carrier K | 3 | F-1 | 25 | 22.9 | S-4 | 75 | 68.8 | C-1 | 9 | 8.3 | 820 |
| Carrier L | 6 | F-1 | 25 | 25.0 | S-1 | 75 | 75.0 | — | 0 | 0.0 | 820 |
| Carrier M | 6 | — | 0 | 0.0 | S-1 | 75 | 89.3 | C-1 | 9 | 10.7 | 820 |
| Carrier N | 6 | F-1 | 25 | 73.5 | — | 0 | 0.0 | C-1 | 9 | 26.5 | 820 |

| Silica carrier | BET specific surface area ($m^2/g$) | Average pore diameter BJH method (nm) | Bulk density (g/L) | Presence of mesopores | Presence of macropores | Pore volume of macropores (cc/g) |
|---|---|---|---|---|---|---|
| Carrier A | 313 | 6.6 | 548 | Yes | Yes | 0.15 |
| Carrier B | 286 | 9.4 | 438 | Yes | Yes | 0.22 |
| Carrier C | 225 | 14.5 | 386 | Yes | Yes | 0.22 |
| Carrier D | 287 | 9.4 | 439 | Yes | Yes | 0.25 |
| Carrier E | 293 | 6.6 | 567 | Yes | Yes | 0.16 |
| Carrier F | 297 | 5.5 | 619 | Yes | Yes | 0.16 |
| Carrier G | 294 | 7.4 | 551 | Yes | Yes | 0.15 |
| Carrier H | 273 | 6.4 | 593 | Yes | Yes | 0.11 |
| Carrier I | 356 | 6.5 | 507 | Yes | Yes | 0.19 |
| Carrier J | 381 | 6.5 | 481 | Yes | Yes | 0.20 |
| Carrier K | 284 | 5.4 | 686 | Yes | Yes | 0.15 |
| Carrier L | Not formable and not usable as a carrier | | | | | |
| Carrier M | | | | | | |
| Carrier N | | | | | | |

TABLE 3

| Number | Silica carrier | Product name of carrier | BET specific surface area (m²/g) | Average pore diameter (BJH method) (nm) | Bulk density (g/L) | Presence of mesopores | Presence of macropores | Pore volume of macropores (cc/g) |
|---|---|---|---|---|---|---|---|---|
| Comp. Carrier Ex. 4 | Carrier P | KA-160 manufactured by Clariant Catalysts | 151 | 10.8 | 579 | Yes | No | (0.19) |
| Comp. Carrier Ex. 5 | Carrier Q | CARiACT Q-15 manufactured by Fuji Silysia | 183 | 22.4 | 430 | Yes | No | 0.02 |
| Comp. Carrier Ex. 6 | Carrier R | CARiACT Q-30 manufactured by Fuji Silysia | 105 | 33.6 | 435 | Yes | No | 0.03 |
| Comp. Carrier Ex. 7 | Carrier S | CARiACT Q-6 manufactured by Fuji Silysia | 379 | 5.2 | 623 | Yes | No | 0.01 |

As is apparent from FIGS. 1 and 2, in the silica carrier A of Production Example 1, mesopores having a peak around 4.5 nm and macropores having a peak around 90 nm are present, and the pore volume of the macropores is 0.15 cc/g. On the other hand, in the silica carriers P and Q of Comparative Carrier Examples 4 and 5, there is no peak corresponding to macropores in FIG. 2.

Tables 2 and 3 show values calculated by integrating the pore volume of the macropores in the range of more than 50 nm and equal to or less than 1000 nm based on the pore diameter distribution by the mercury intrusion method. The pore volumes of the macropores of the silica carriers A to K in Production Examples are 0.10 cc/g or more, while the pore volumes of the macropores of the silica carriers Q to S in Comparative Carrier Examples 5 to 7 are only 0.03 cc/g or less, and there is no macropore. In addition, although the silica carrier P of Comparative Carrier Example 4 is calculated to have a pore volume of macropores of 0.19 cc/g, there is substantially no macropore since no clear macropore peak is observed in FIG. 2.

Example 1

In a 100 mL beaker, 40.7 g of a commercially available Keggin silicotungstic acid 26 hydrate ($H_4SiW_{12}O_{40} \cdot 26H_2O$; manufactured by Nippon Inorganic Colour & Chemical Co., Ltd.) was weighed, a small amount of distilled water was added to solve silicotungstic acid, and then the solution was transferred to a 200 mL graduated cylinder. Then, distilled water was added so that the liquid amount of the silicotungstic acid solution in the graduated cylinder was 95% of the water absorption rate of a carrier to be used, and the mixture was stirred so that the entire mixture was uniform. After stirring, the aqueous solution of silicotungstic acid was transferred to a 200 mL volumetric flask, and then weighed 100 mL of the silica carrier A was put into the 200 mL volumetric flask, and the contents of the volumetric flask were mixed so that the aqueous solution of silicotungstic acid contacted the entire carrier. The silica carrier A on which silicotungstic acid was supported was transferred to a porcelain dish, air-dried for one hour, and then dried for 5 hours in a hot air dryer adjusted to 130° C. After drying, the carrier was transferred into a desiccator and cooled to room temperature to obtain a catalyst A for producing an alcohol. The supported amount of the catalyst was 64 parts by mass with respect to 100 parts by mass of the carrier.

25 mL of the obtained catalyst A was weighed, and filled in a tubular reactor (made from SUS316, inner diameter 10 mm, length 300 mm), which was then pressurized to 0.75 MPaG after nitrogen gas replacement. Then, the reactor was heated to 160° C., and at a stage where the temperature was stable, amounts of water and ethylene so that the molar ratio of water to ethylene was 0.4 were supplied to the reactor at a GHSV (gas space velocity) of 2000/hr to carry out a hydration reaction of ethylene. After the supply of water and ethylene, the temperature of the reactor was adjusted so that the peak temperature of the catalyst layer reached 190° C. after the temperature was stable. At 2 hours after the peak temperature was stabilized at 190° C., a gas passed through the reactor was cooled, and sampling of a condensate and a reaction gas from which the condensate was removed was carried out for 1 hours. Reaction results of the catalyst A were calculated based on the masses of the obtained condensate and reaction gas, the gas flow rates, and analysis results. Table 4 shows the reaction results.

TABLE 4

| | Catalyst number | Carrier number | Catalyst specific surface area (m²/mL) | Ethylene conv. rate (%) | Ethanol STY (g/hr · L) | Ethanol Selectivity (%) | Diethyl ether STY (g/hr · L) | Diethyl ether Selectivity (%) |
|---|---|---|---|---|---|---|---|---|
| Ex. 1 | Catalyst A | Carrier A | 148.1 | 5.7 | 79 | 59 | 72 | 41 |
| Ex. 2 | Catalyst B | Carrier B | 120.9 | 5.0 | 68 | 51 | 58 | 51 |
| Ex. 3 | Catalyst C | Carrier C | 98.3 | 4.0 | 65 | 54 | 43 | 45 |
| Ex. 4 | Catalyst D | Carrier D | 156.3 | 4.8 | 74 | 52 | 54 | 47 |
| Ex. 5 | Catalyst E | Carrier E | 143.3 | 6.2 | 83 | 45 | 79 | 54 |
| Ex. 6 | Catalyst F | Carrier F | 159.9 | 6.3 | 85 | 46 | 80 | 54 |
| Ex. 7 | Catalyst G | Carrier G | 138.7 | 6.6 | 89 | 46 | 83 | 53 |
| Ex. 8 | Catalyst H | Cartier H | 147.3 | 6.7 | 88 | 45 | 87 | 55 |
| Ex. 9 | Catalyst I | Carrier I | 186.5 | 6.6 | 85 | 44 | 86 | 56 |
| Ex. 10 | Catalyst J | Carrier J | 192.3 | 6.3 | 84 | 46 | 80 | 54 |
| Ex. 11 | Catalyst K | Carrier K | 145.6 | 5.9 | 78 | 45 | 76 | 54 |

TABLE 4-continued

|  | Catalyst number | Carrier number | Catalyst specific surface area (m²/mL) | Ethylene conv. rate (%) | Ethanol STY (g/hr · L) | Ethanol Selectivity (%) | Diethyl ether STY (g/hr · L) | Diethyl ether Selectivity (%) |
|---|---|---|---|---|---|---|---|---|
| Comp. Ex. 1 | Catalyst P | Carrier P | 79.4 | 2.7 | 52 | 65 | 23 | 35 |
| Comp. Ex. 2 | Catalyst Q | Carrier Q | 94.1 | 3.1 | 60 | 66 | 25 | 34 |
| Comp. Ex. 3 | Catalyst R | Cartier R | 59.2 | 2.5 | 50 | 69 | 18 | 31 |

Examples 2 to 11 and Comparative Examples 1 to 3

Catalysts B to K, and Comparative Catalysts P to R were prepared using the silica carriers B to K described in Table 2 and the silica carriers P to R described in Table 3 in the same manner as in Example 1. The hydration reaction of ethylene was carried out in the same manner as in Example 1 with respect to each catalyst. Table 4 shows reaction results.

Example 12

In a 100 mL beaker, 50.0 g of a commercially available Keggin silicotungstic acid 26 hydrate ($H_4SiW_{12}O_{40} \cdot 26H_2O$; manufactured by Nippon Inorganic Colour & Chemical Co., Ltd.) and 0.10 g of lithium nitrate were weighed, a small amount of distilled water was added to solve silicotungstic acid and lithium nitrate, and then the solution was transferred to a 200 mL graduated cylinder. Then, distilled water was added so that the liquid amount of the mixed solution of silicotungstic acid and lithium nitrate in the graduated cylinder was 95% of the water absorption rate of a carrier to be used, and the mixture was stirred so that the entire mixture was uniform. After stirring, the aqueous solution of silicotungstic acid and lithium nitrate was transferred to a 200 mL volumetric flask, and then weighed 100 mL of the silica carrier B of Production Example 2 was put into the 200 mL volumetric flask, and the contents of the volumetric flask were mixed so that the aqueous solution of silicotungstic acid and lithium nitrate contacted the entire carrier. The silica carrier B on which a lithium salt of silicotungstic acid ($Li_{0.1}H_{3.9}SiW_{12}O_{40}$) was supported was transferred to a porcelain dish, air-dried for one hour, and then dried for 5 hours in a hot air dryer adjusted to 130° C. After drying, the carrier was transferred into a desiccator and cooled to room temperature to obtain a catalyst O for producing an alcohol. The supported amount of the catalyst was 80 parts by mass with respect to 100 parts by mass of the carrier.

25 mL of the obtained catalyst O was weighed, and filled in a tubular reactor (made from SUS316, inner diameter 10 mm, length 300 mm), which was then pressurized to 2.0 MPaG after nitrogen gas replacement. Then, the reactor was heated to 160° C., and at a stage where the temperature was stable, amounts of water and ethylene so that the molar ratio of water to ethylene was 0.3 were supplied to the reactor at a GHSV (gas space velocity) of 4000/hr to carry out a hydration reaction of ethylene. The reaction gas passed through the reactor was cooled and separated into a condensed component and a reaction gas, which is a non-condensed component containing diethyl ether as a by-product, and the separated reaction gas was recycled to the reactor while partially purging so that an inert component did not accumulate. By recycling diethyl ether to the reactor, the concentrations of the reactor inlet and outlet were the same due to the relationship of the reaction equilibrium. Further, after the supply of water and ethylene, the temperature of the reactor was adjusted so that the peak temperature of the catalyst layer reached 210° C. after the temperature was stable. At 2 hours after the peak temperature was stabilized at 210° C., a gas passed through the reactor was cooled, and sampling of a condensate and a reaction gas from which the condensate was removed was carried out for 1 hours. Reaction results of the catalyst O were calculated based on the masses of the obtained condensate and reaction gas, the gas flow rates, and analysis results. Table 5 shows the reaction results and evaluation conditions.

Comparative Example 4

A comparative catalyst S was prepared in the same manner as in Example 12, except that CARiACT Q-6 (carrier S), a silica carrier manufactured by Fuji Silysia Chemical Ltd., was used as a silica carrier, and the reaction evaluation of the catalyst was carried out. Table 5 shows reaction results and evaluation conditions.

TABLE 5

|  | Catalyst number | Silica carrier number | Reaction temperature *1 (° C.) | Reaction pressure (MPaG) | GHSV (/hr) | Ethylene conv. (%) | Ethanol STY (g/hr/L) |
|---|---|---|---|---|---|---|---|
| Ex. 12 | Catalyst O | Carrier B | 210 | 2 | 4000 | 4.1 | 249 |
| Comp. Ex. 4 | Catalyst S | Carrier S |  |  |  | 3.4 | 207 |

*1: Peak temperature of catalyst layer

INDUSTRIAL APPLICABILITY

According to the present disclosure, there is provided a supported catalyst for producing an alcohol by a hydration reaction of an olefin by supporting a heteropolyacid or a salt of the heteropolyacid salt on a particular carrier. Further, according to the present disclosure, in the method for producing ethanol from ethylene using the catalyst for producing an alcohol, it is possible to provide a highly efficient ethanol production method by a method for recycling diethyl ether into a reactor, which is industrially useful.

The invention claimed is:

1. A method for producing an alcohol comprising
kneading a fumed silica obtained by a combustion method, a silica gel obtained by a gel method, and a colloidal silica obtained by a sol-gel method or a water glass method,
forming the obtained kneaded material, and
then calcining the obtained shaped body to form a silica carrier,
supporting a heteropolyacid or a salt thereof on the silica carrier to form a solid acid catalyst, and
supplying water and an olefin having 2 to 5 carbon atoms to a reactor filled with the solid acid catalyst and subjecting them to a hydration reaction in a gas phase,
wherein a blending amount of the fumed silica is 5 to 50 parts by mass, a blending amount of the silica gel is 40 to 90 parts by mass, and a blending amount of a solid content of the colloidal silica is 5 to 30 parts by mass, based on total parts by mass of the silica carrier.

2. The method for producing an alcohol according to claim 1, wherein the calcining temperature is 300 to 1000° C.

3. The method for producing an alcohol according to claim 1, wherein the heteropolyacid is at least one compound selected from the group consisting of silicotungstic acid, phosphotungstic acid, phosphomolybdic acid, silicomolybdic acid, silicovanadotungstic acid, phosphovanadotungstic acid, and phosphovanadomolybdic acid.

4. The method for producing an alcohol according to claim 1, wherein the silica carrier has mesopores having a pore diameter of 2 to 50 nm and macropores having a pore diameter of more than 50 nm and not more than 1000 nm in a pore diameter distribution measurement.

5. The method for producing an alcohol according to claim 4, wherein in the pore diameter distribution by the mercury intrusion method, the pore volume of the macropores of the silica carrier is 0.05 to 0.50 cc/g.

6. The method for producing an alcohol according to claim 4, wherein the BET specific surface area of the silica carrier is 200 to 500 $m^2/g$.

7. The method for producing an alcohol according to claim 4, wherein the bulk density of the silica carrier is 300 to 750 g/L.

8. The method for producing an alcohol according to claim 4, wherein the average pore diameter of the mesopores of the silica carrier by the BJH method is 3 to 16 nm.

9. The method for producing an alcohol according to claim 4, wherein the particle diameter of the silica carrier is 0.5 to 12 mm.

10. The method for producing an alcohol according to claim 4, wherein the heteropolyacid is at least one compound selected from the group consisting of silicotungstic acid, phosphotungstic acid, phosphomolybdic acid, silicomolybdic acid, silicovanadotungstic acid, phosphovanadotungstic acid, and phosphovanadomolybdic acid.

11. The method for producing an alcohol according to claim 4, wherein the olefin having 2 to 5 carbon atoms is ethylene and the alcohol produced by the hydration reaction is ethanol.

12. The method for producing an alcohol according to claim 11, wherein an ether compound by-produced by the hydration reaction of ethylene is recycled into the reactor.

* * * * *